(12) United States Patent  
Higgins et al.

(10) Patent No.: US 7,731,030 B2  
(45) Date of Patent: Jun. 8, 2010

(54) SUPPOSITORY DELIVERY DEVICE

(75) Inventors: Karen D. Higgins, Richmond, VA (US); Kathleen K. Pieper, Midlothian, VA (US)

(73) Assignee: Just Like Sisters, LLC, Midlothian, VA (US)

( * ) Notice: Subject to any disclaimer, the term of this patent is extended or adjusted under 35 U.S.C. 154(b) by 264 days.

(21) Appl. No.: 12/041,771

(22) Filed: Mar. 4, 2008

(65) Prior Publication Data

US 2009/0223855 A1  Sep. 10, 2009

(51) Int. Cl.  
*B65D 83/04* (2006.01)

(52) U.S. Cl. .......................... 206/529; 53/492; 424/433; 424/DIG. 15; 514/966

(58) Field of Classification Search ................ 206/438, 206/440, 441, 529, 539, 570; 53/453, 492; 424/433, 436, 659, DIG. 15; 514/177, 282, 514/420, 965, 966; 604/385.02, 385.18, 604/12, 279

See application file for complete search history.

(56) References Cited

U.S. PATENT DOCUMENTS

| | | | | |
|---|---|---|---|---|
| 3,039,246 A | * | 6/1962 | David | 206/529 |
| 3,058,469 A | * | 10/1962 | Crockford | 604/385.18 |
| 3,113,672 A | * | 12/1963 | Brown | 206/529 |
| 3,135,262 A | * | 6/1964 | Kobler et al. | 604/385.18 |
| 3,993,073 A | | 11/1976 | Zaffaroni | |
| 4,174,040 A | * | 11/1979 | Wang | 206/529 |
| 6,010,001 A | * | 1/2000 | Osborn, III | 206/440 |
| 6,364,854 B1 | | 4/2002 | Ferrer et al. | |
| 6,712,784 B2 | | 3/2004 | Huang | |
| 7,081,110 B2 | | 7/2006 | Karapasha | |
| 2002/0026157 A1 | | 2/2002 | Fournier | |
| 2006/0088588 A1 | | 4/2006 | Pila-Collazo | |

* cited by examiner

*Primary Examiner*—Luan K Bui  
(74) *Attorney, Agent, or Firm*—McNees Wallace & Nurick

(57) ABSTRACT

A suppository delivery device that allows for the insertion of a suppository without having contact with the suppository or rectum. The suppository delivery device includes a stabilizer to which the suppository is mounted, and a package, which protects the user's hands and fingers from the suppository and rectum and prevents germs from contacting the suppository before being inserted into the rectum.

20 Claims, 1 Drawing Sheet

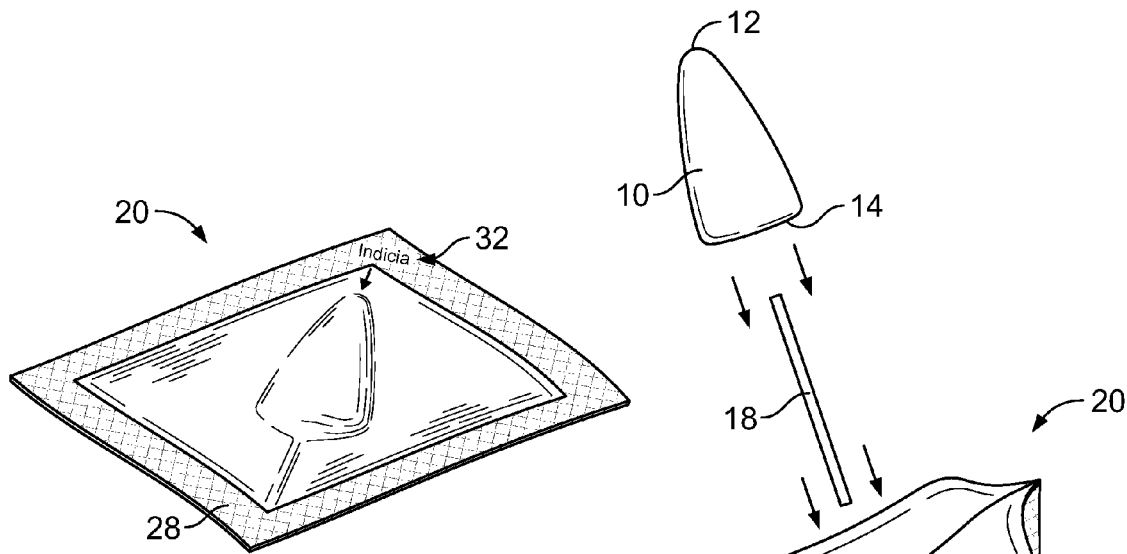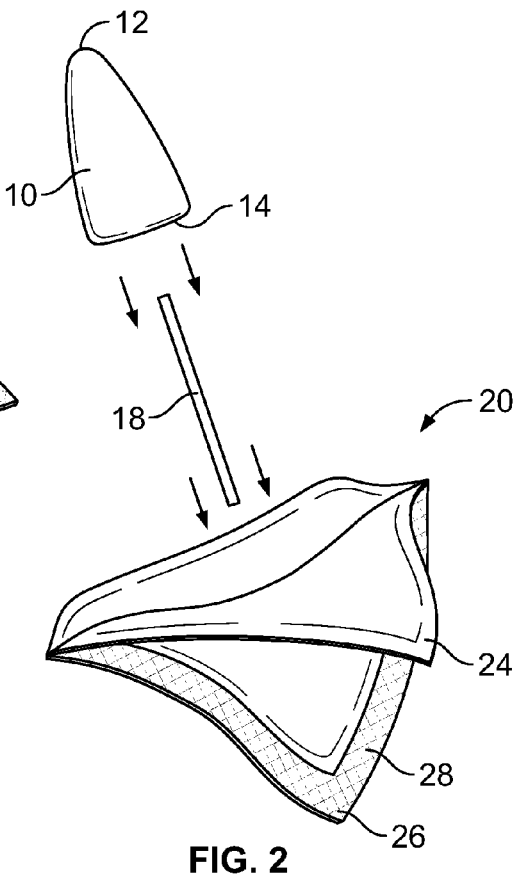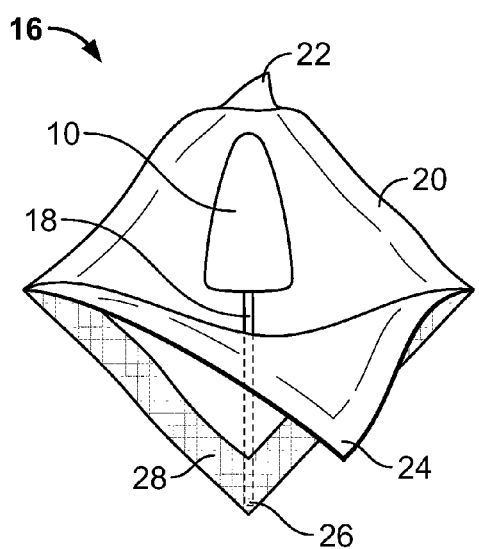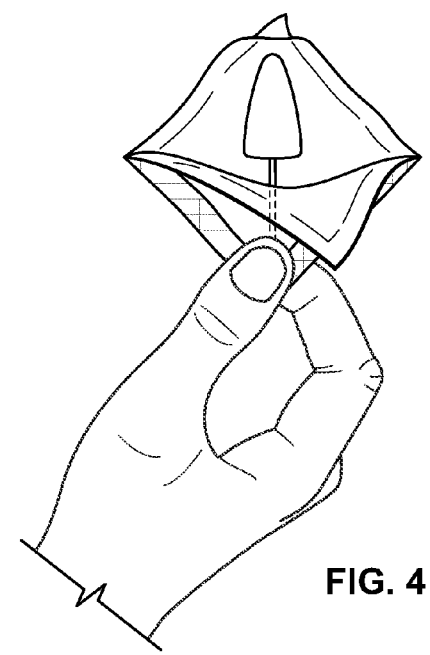
FIG. 1
FIG. 2
FIG. 3
FIG. 4

SUPPOSITORY DELIVERY DEVICE

FIELD OF THE INVENTION

The present application is directed to a suppository delivery device and more specifically, to a suppository delivery device that eliminates direct contact with a suppository and/or the rectum during delivery of the suppository.

A rectal suppository is a systemically acting or locally acting drug delivery system that is inserted into the rectum. There are many reasons for having to use a suppository, for example, suppositories are used for patients when the patient has a vomiting tendency, when the particular drug administered causes an upset stomach when taken orally, or when a patient is too sick to accept an orally administered drug. In addition, some types of drugs, or some illnesses require a suppository administration and are not available in any other form.

Generally, a suppository is a solid when inserted and dissolves inside the body to deliver medication to the bloodstream. Rectal suppositories are commonly used for laxative purposes and made of chemicals such as glycerin or bisacodyl to treat hemorrhoids by delivering a moisturizer or vasoconstrictor. Suppositories may also be used for the delivery of many other systemically-acting medications for general medical administration purposes, such as promethazine or aspirin.

Typically, the use of an examination glove or a finger cot eases insertion of the suppository by protecting the rectal wall and the fingernail(s) from each other. Further, some suppositories are made with a greasy base, such as cocoa butter, in which the active ingredient and other excipients are dissolved. The base used is designed to melt at body temperature. Other suppositories are made from a water soluble base, such as polyethylene glycol, or glycerin, which dissolves/melts at body temperature as well.

Since suppositories are designed to melt at body temperature or to dissolve with bodily contact, it is desirable to reduce contact of the suppository with any body part other than the rectum so that none of the medicine is wasted before insertion. In addition, these ingredients (mentioned above) can be messy and easily get on the user's hands, fingers, or any object the suppository comes into contact with, thereby contaminating the suppository and making a mess in the process.

Therefore, it would be advantageous to have a suppository delivery device that provides for the insertion of a rectal suppository with substantially no contact with any part of the user's body other than the rectum. Further, it would be advantageous to have a suppository delivery device that aids in the delivery process. Intended advantages of the disclosed systems satisfy one or more of these needs or provide other advantageous features. Other features and advantages will be made apparent from the present specification. The teachings disclosed extend to those embodiments that fall within the scope of the claims, regardless of whether they accomplish one or more of the aforementioned needs.

SUMMARY OF THE INVENTION

A suppository delivery device in accordance with one embodiment of the application is disclosed, having a suppository having a first end and a second end adjacent the first end. The suppository delivery device also has a stabilizer being removably secured in the suppository through the second end and a package having a first side and a second side, the suppository and stabilizer being disposed between the first side and second side and surrounded by the package. The package is configured such that, when in a partially opened position, the package forms a shield exposing the suppository on an opposite side of the shield of a still closed portion of the packaging. One advantage of the device is the clean delivery of a suppository without having contact with any body part other than the rectum.

Another embodiment of the present application includes a suppository delivery device having a rectal suppository having a first end and a second end adjacent the first end, a stabilizer being a predetermined length and having a first end and a second end, the first end of the stabilizer being removably secured to the second end of the suppository, and a package having a first side and a second side, the suppository and stabilizer being disposed between the first side and second side and surrounded by the package. The package is configured such that, when in a partially opened position, the package forms a shield exposing the suppository on an opposite side of the shield of a still closed portion of the packaging.

A method for inserting a suppository with a suppository delivery device in accordance with aspects of the present application includes several steps. The first step is providing a suppository delivery device, the suppository delivery device having a suppository having a first end and a second end adjacent the first end, a stabilizer being secured into the suppository through the second end and a package having a first side and a second side, the suppository and stabilizer being disposed between the first side and second side and surrounded by the package. The method also includes the step of exposing the suppository by partially removing the first side and partially removing the second side, the partially removed first side and the partially removed second side form a shield. The next step of the method includes inserting the suppository, and removing the stabilizer and package, the stabilizer disengaging from the suppository.

An advantage is that the device protects the user from getting potentially harmful ingredients on their hands and other body parts.

Another advantage is the protection of the suppository from germs on the user's hands.

Yet another advantage of the device is a stabilizer unit that aids in the delivery process of the suppository.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 1 illustrates an example of the suppository delivery device in the sealed package in accordance with aspects of the invention;

FIG. 2 illustrates an exploded view of the suppository delivery device;

FIG. 3 illustrates the suppository delivery device with the package prepared for insertion in accordance with aspects of the invention;

FIG. 4 illustrates the suppository delivery device as held by the user in accordance with aspects of the invention; and Wherever possible, the same reference numbers will be used throughout the drawings to refer to the same or like parts.

DETAILED DESCRIPTION OF EXEMPLARY EMBODIMENTS

A typical suppository is sealed in packaging for sanitary reasons to maintain a sterile product. A user must open the packaging to reach the suppository, and then handle the suppository with the user's hands or fingers. Opening the packaging on typical suppositories may be difficult, causing the suppository to fall onto the floor or other surface, and thereby contaminate the suppository. Further, traditionally a rectal suppository is inserted into a rectum with a user's finger and because a suppository is made from a waxy or other similar substance that easily melts or disintegrates, often the finger and/or hands get the suppository substance on them. This is a problem because the insertion of the suppository becomes a messy process and because germs from the finger or hands may be transferred to the suppository before being inserted into the rectum.

Rectal suppositories typically are shaped like a bullet, where one end is flat or blunt and the other end is rounded, or pointed. The blunt end is inserted into the rectum first, with the finger pushing on the rounded end. This can be a problem because it is difficult to have a firm grasp on the suppository during insertion, causing the suppository to fall before or during insertion and causing the insertion process to be difficult. Because of these issues with insertion, it is often easier for a second party to insert the suppository for the user. Because of privacy and embarrassment issues, many users are not comfortable with a second party inserting the suppository into their rectum, leaving them to attempt to insert the suppository themselves.

One embodiment of a suppository delivery device 16 in accordance with an exemplary embodiment is shown in FIG. 1, having a diamond or square shaped package or packaging 20. The package 20 may be two pieces or sides or material that are sealed or otherwise fastened together to form a pocket or retention area for the suppository delivery device 16. The package 20, or both sides of the package may be a pliable material made of co-extruded backing film and a polyester release liner. For example, each side of the package 20 would contain the co-extruded backing film and a polyester release liner. The two sides would be fastened or sealed together with the polyester release liner of one side facing the polyester release liner of the second side, so that the suppository delivery device 16 is contacting only the polyester release lining when disposed in the packaging 20. The package 20, and each side of the package 20, may be made from any other suitable material and may be any other suitable shape as well. For example, the packaging may be round. The package 20 may have various indicia 32 on the outside of the package 20. For example, the package 20 may have indicia 32 to show the user which direction to open the package 20, indicia to instruct the user where to place their hands or fingers on the package 20, and indicia 32 to instruct the user how to peel the package 20 for use. While these examples have been given for specific indicia 32 on the package 20, it is known by those of ordinary skill in the art that any indicia may be used. The suppository 10 is mounted to a first end 30 of a stabilizer 18 (as shown in FIGS. 2 and 3) and sealed or otherwise fastened in the package 20.

FIG. 3 illustrates another view of the suppository delivery device 16. The packaging 20 is opened by peeling back two corners 22, 24 of the packaging 20 while firmly holding the still sealed opposite corners 26 between two fingers (shown in FIG. 4). When the two corners 22, 24 are peeled back, the suppository 10 is exposed and ready for insertion. The peeled back corners 22, 24 of the packaging 20 form a shield for the user's fingers and hands, protecting them from touching the suppository 20 and also from having contact with the user's rectum or other body parts during insertion. The stabilizer 18 is disposed inside the suppository 10 and extends from the suppository 10 and into the opposite corner 26 of the packaging 20. Therefore, when the user is firmly holding the opposite corner 26 of the packaging 20, the user is also holding a second end of the stabilizer 18 through the packaging 20.

Referring back to FIG. 2, an exploded view of an embodiment of the suppository delivery device 16 is shown. The suppository 10 is mounted on the stabilizer 18 at the blunt end 14. The stabilizer 18 may be a thin piece of stiff or substantially rigid material such as a wire, plastic rod or other similar material. The stabilizer 18 may also be a semi-rigid material able to bend slightly to provide a more comfortable insertion of the suppository 10 into the user's rectum. While wire and plastic have been used as examples, it is known by one of ordinary skill in the art that any type of suitable material may be used for the stabilizer 18. The suppository 10 is made of a waxy or other similar substance, thus the suppository 10 may be secured to the stabilizer 18 by operation of the properties of the material in the suppository 10. The suppository 10 is secured to the stabilizer 18 such that the suppository 10 does not readily fall from the stabilizer 18, but once inserted into the rectum, the suppository 10 easily detaches from the stabilizer 18 and remains in the rectum. Once the suppository 10 is secured in the rectum of the user, the packaging 20 and stabilizer 18 may be discarded.

The stabilizer 18 may be secured to the packaging 20 with glue, adhesive or other similar substance to ensure that the stabilizer 18 does not fall from the packaging 20. In addition, another embodiment may include the stabilizer 18 as secured in the packaging 20 by the sealing process that seals the package 20 during manufacture, wherein the end of the stabilizer 18 is disposed in the edge 28 of the package 20, as shown in FIG. 3. The stabilizer 18 may also be disposed within the package 20, and secured in place by a force applied by the user's hands (FIG. 4) once the package 20 is opened.

Another embodiment of the suppository delivery device 16 includes the suppository 10 attached to the stabilizer 18 at the rounded end 12. Yet another embodiment of the suppository delivery device 16 may include use with vaginal suppositories or urethral suppositories.

Yet another embodiment of the suppository delivery device 16 includes the stabilizer 18 being a predetermined length to prevent over insertion of the suppository 10 or the stabilizer 18. Over insertion of the suppository 10 and/or the stabilizer 18 could cause tearing of the rectal walls and tissues, thereby harming the user. By having the stabilizer 18 at a predetermined length, over insertion can be avoided. Further, another embodiment of the suppository delivery device 16 may include the stabilizer 18 having blunt or rounded ends. The round or blunt ends will minimize, reduce, or substantially eliminate the danger of the stabilizer 18 puncturing the wall or lining of the rectum upon insertion. In addition, since the suppository 10 is made of a waxy and slippery substance, it is possible that the suppository 10 may slide off of the stabilizer 18. In the event the suppository 10 slides off of the stabilizer, 18 the rounded or blunt end of the stabilizer 18 will minimize, reduce, or substantially eliminate the danger of the stabilizer 18 puncturing the wall or lining of the rectum.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A suppository delivery device comprising:
    a suppository having a first end and a second end adjacent the first end;
    a stabilizer being removably secured in the suppository through the second end;
    a package having a first side and a second side, the suppository and stabilizer being disposed between the first side and second side and surrounded by the package; and
    wherein the package is configured such that, when in a partially opened position, the package forms a shield exposing the suppository on an opposite side of the shield of a still closed portion of the packaging.

2. The suppository delivery device of claim 1 wherein the first end of the suppository is blunt.

3. The suppository delivery device of claim 1 wherein the second end of the suppository is rounded.

4. The suppository delivery device of claim 1 wherein the package is diamond or square shaped.

5. The suppository delivery device of claim 4 wherein when the package is partially removed, the corner of the first side and the corresponding corner of the second side are pulled apart and pulled downward.

6. The suppository delivery device of claim 1 wherein the stabilizer is secured in the package.

7. The suppository delivery device of claim 6 wherein the stabilizer is secured in the package with an adhesive.

8. The suppository delivery device of claim 1 wherein the stabilizer is substantially rigid.

9. The suppository delivery device of claim 1 wherein the suppository is a rectal suppository.

10. The suppository delivery device of claim 1 wherein the stabilizer has a predetermined length.

11. The suppository delivery device of claim 1 wherein the stabilizer has two ends, and wherein at least one end of the two ends is blunt or rounded.

12. A suppository delivery device comprising:
    a rectal suppository having a first end and a second end adjacent the first end;
    a stabilizer being a predetermined length and having a first end and a second end, the first end of the stabilizer being removably secured to the second end of the suppository;
    a package having a first side and a second side, the suppository and stabilizer being disposed between the first side and second side and surrounded by the package; and
    wherein the package is configured such that, when in a partially opened position, the package forms a shield exposing the suppository on an opposite side of the shield of a still closed portion of the packaging.

13. The suppository delivery device of claim 12 wherein the first end of the rectal suppository is flat.

14. The suppository delivery device of claim 12 wherein the second end of the rectal suppository is rounded.

15. The suppository delivery device of claim 14 wherein the user holds the stabilizer secure in the package.

16. The suppository delivery device of claim 12 wherein the stabilizer is secured in the package.

17. The suppository delivery device of claim 12 wherein the stabilizer is substantially rigid.

18. A method for inserting a suppository with a suppository delivery device comprising the steps of:
    providing a suppository delivery device, the suppository delivery device further comprising:
        a suppository having a first end and a second end adjacent the first end;
        a stabilizer being secured into the suppository through the second end;
        a package having a first side and a second side, the suppository and stabilizer being disposed between the first side and second side and surrounded by the package;
    exposing the suppository by partially removing the first side and partially removing the second side, the partially removed first side and the partially removed second side form a shield;
    inserting the suppository; and
    removing the stabilizer and package, the stabilizer disengaging from the suppository.

19. The method of claim 18 wherein the step of partially removing the first side and partially removing the second side further comprises separating a portion of the first side from a portion of the second side and the portion of the first side and the corresponding portion of the second side are pulled apart and pulled downward.

20. The method of claim 18 wherein the step of providing a suppository delivery device further comprises holding a portion of the package in a user's hand.

* * * * *